(12) United States Patent
McCray

(10) Patent No.: US 8,298,202 B2
(45) Date of Patent: Oct. 30, 2012

(54) MALE URINARY DEVICE

(76) Inventor: Risa Culp McCray, Clarksville, PA (US)

( * ) Notice: Subject to any disclaimer, the term of this patent is extended or adjusted under 35 U.S.C. 154(b) by 856 days.

(21) Appl. No.: 12/203,255

(22) Filed: Sep. 3, 2008

(65) Prior Publication Data

US 2009/0069765 A1 Mar. 12, 2009

Related U.S. Application Data

(60) Provisional application No. 60/967,990, filed on Sep. 10, 2007.

(51) Int. Cl.
*A61F 5/44* (2006.01)

(52) U.S. Cl. .................................. 604/349; 604/385.03

(58) Field of Classification Search .................. 604/349, 604/317, 327, 345, 346, 347, 385.01, 385.03, 604/386, 387

See application file for complete search history.

(56) References Cited

U.S. PATENT DOCUMENTS

| | | | |
|---|---|---|---|
| 3,403,410 A * | 10/1968 | Benzel et al. .................. | 4/144.2 |
| 3,583,402 A | 6/1971 | Cordell et al. | |
| 4,453,938 A | 6/1984 | Brendling | |
| 4,601,716 A | 7/1986 | Smith | |
| 4,790,835 A | 12/1988 | Elias | |
| 4,863,448 A | 9/1989 | Berg | |
| 5,354,132 A * | 10/1994 | Young et al. .................... | 383/49 |
| 5,643,235 A | 7/1997 | Figuerido | |
| 5,695,485 A | 12/1997 | Duperret et al. | |
| 6,338,729 B1 * | 1/2002 | Wada et al. .............. | 604/385.09 |
| 6,479,726 B1 | 11/2002 | Cole | |
| 6,949,090 B1 * | 9/2005 | Leers et al. .................... | 604/386 |
| 7,658,194 B2 * | 2/2010 | Anderson et al. ............. | 128/885 |
| 2003/0004478 A1 * | 1/2003 | Mattsson ....................... | 604/349 |
| 2004/0038008 A1 * | 2/2004 | Levine et al. ................. | 428/189 |

* cited by examiner

*Primary Examiner* — Tatyana Zalukaeva
*Assistant Examiner* — Benedict L Hanrahan
(74) *Attorney, Agent, or Firm* — The Webb Law Firm

(57) ABSTRACT

A urinary device for use on a penis of a male suffering from urinary incontinence. The device comprises a body having a closed distal end and an open proximal end and defining a cavity therein. The body has an inner layer made of a moisture absorbent material and an outer layer made of a moisture resistant material. A malleable material encircles a portion of the proximal end of the body wherein the proximal end is adapted to conform to the shape of the malleable material.

18 Claims, 4 Drawing Sheets

US 8,298,202 B2

MALE URINARY DEVICE

CROSS REFERENCE TO RELATED APPLICATIONS

This application claims the benefit of U.S. Provisional Patent Application No. 60/967,990, filed Sep. 10, 2007, which is hereby incorporated by reference.

BACKGROUND OF THE INVENTION

1. Field of the Invention

The present invention relates to sanitary devices and, more particularly, to a urinary device for use by incontinent males to contain and absorb urine.

2. Description of Related Art

The use of devices to collect and contain urine for incontinent adults is well-known in the art. Such devices are typically large diapers or absorbent pads which are bulky, cumbersome to use, difficult to put on and oftentimes uncomfortable for the individual. Specifically, males who are suffering from urinary incontinence oftentimes have no choice but to use these large diapers or absorbent pads because they are readily available in the marketplace. These large diapers or pads cover both the penis and rectum in males who are totally incontinent and who cannot control any of their excretory functions. However, there is a need for a device that can be used on incontinent males suffering only from urinary incontinence. Such absorbing devices that cover the penis of males are also known in the art. See, for example, U.S. Pat. Nos. 3,583,402; 4,453,938; 4,601,716; 4,790,835; 4,863,448; 5,643,235; 5,695,485 and 6,479,726. All of these prior art devices are designed to cover the penis of incontinent males. However, there are several disadvantages in the use of these prior devices. For example, these prior art devices are difficult to fasten and/or re-fasten to the penis of the user.

The prior art devices are generally tubular devices that either use an elastomeric material such as an elastic band, an adhesive such as tape or a hook and loop fastener such as Velcro® at one end to fasten the device onto the penis. With all of these prior art devices, it takes both hands of a person, either the user or the user's aid, to insert properly onto a penis and fasten the device thereon using adhesive or Velcro® fasteners. When an elastic band is used at the open end of the device, two hands are generally needed to stretch the opening in order for the device to be inserted onto the penis. Depending on the size (i.e., diameter) of the penis and the strength of the elastomeric material, the closure may be too tight thus making the user uncomfortable and possibly cause circulation problems, or too loose such that the device does not stay on and fails. Although U.S. Pat. No. 4,863,448 discloses a device that has a ring on an upper end to facilitate opening of the device for easy insertion onto a penis, an adhesive is still used to secure the device to the penis, which takes two hands, one hand to hold the device and another to fasten the tape or Velcro®.

It is, therefore, desirable to overcome the above-mentioned problems of the prior art by providing a urinary device for use on incontinent males that is quick and easy to fasten and/or re-fasten to the penis using only one hand. It is also desirable to provide a urinary device wherein the amount of pressure on the penis at the fastening end of the device can be easily adjusted and/or re-adjusted. Further, it is desirable to provide a urinary device wherein the device may be applied and/or re-applied without having to touch or come in contact with the user's penis. Lastly, it is desirable to provide a urinary device wherein the open end will remain in an opened position without any assistance of a user's hand.

SUMMARY OF THE INVENTION

The present invention provides for a urinary device for use on a penis of a male suffering from urinary incontinence. The device comprises a body having a closed distal end and an open proximal end and defining a cavity therein. The body has an inner layer made of a moisture absorbent material and an outer layer made of a moisture resistant material. A malleable material encircles a portion of the proximal end of the body wherein the proximal end is adapted to conform to the shape of the malleable material.

BRIEF DESCRIPTION OF THE DRAWING(S)

DESCRIPTION OF THE PREFERRED EMBODIMENTS

Figure 1:
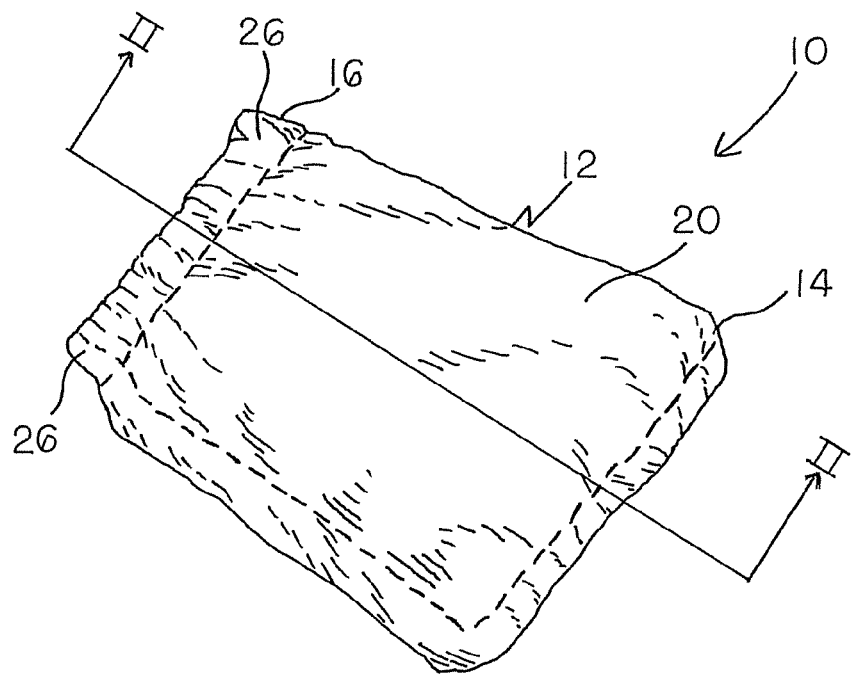
FIG. 1 is a perspective view of a male urinary device made in accordance with the present invention.
Figure 4:
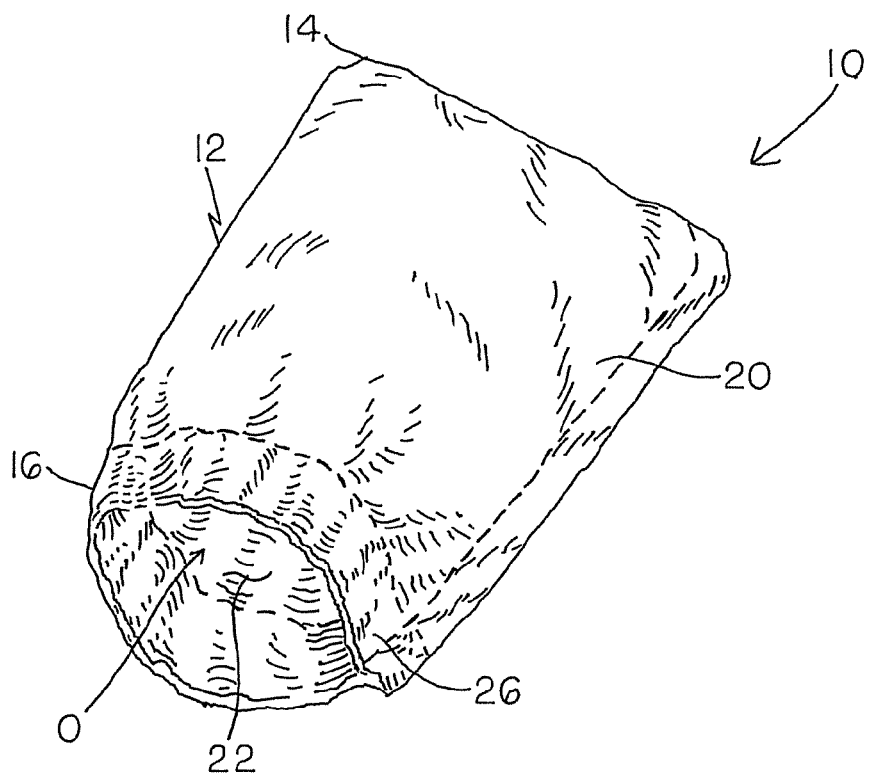
FIG. 4 is a perspective view of the male urinary device shown in FIG. 1 in an opened position.

Referring to FIGS. 1-4, a male urinary device 10 is shown according to the present invention that is used to house a penis of an incontinent male. The device 10 includes a body 12 having a closed lower or distal end 14 and an open upper or proximal end 16 and defining a cavity 22 (shown in FIGS. 2 and 4) therein. The body 12 further includes an inner layer 18 (shown in FIGS. 2 and 3) made of absorbent material and an outer layer 20 made of moisture resistant or hydrophobic material which prevents any urine from escaping from the inner layer 18. The absorbent material of the inner layer 18 may be selected from any of the well known absorbent materials, for example, cotton or any of the synthetic hydrophilic material known in the art. The moisture resistant material of the outer layer 20 can be formed of a woven fabric, a natural fiber, a synthetic fabric or a non-woven material such as a plastic film of a suitable resin. When the outer layer 20 is formed of a woven fiber, preferably, the material is coated or impregnated with a water-resistant coating which imparts moisture impermeability to the fabric. Such two-layered material is well-known in the art and is commonly used to construct commercially available sanitary napkins, disposable diapers, and the like. However, the device 10 can have any number of layers bonded together to improve the absorbency of the device 10 including, but not limited to, adding additional absorbent material into the cavity 22 for extra absorbency.

With continued reference to FIGS. 1-4, the device 10 is generally rectangular in shape in its packaged or un-wrapped form as shown in FIG. 1. The body 12 of the device 10 is preferably made from a rectangular unitary piece of absorbent material or a pad, wherein the piece is folded and attached along its edges, except for the proximal end 16, thus forming a substantially flat piece. Attaching the edges of the pad can be accomplished using any known means in the art such as sewing, applying adhesive or fusing the edges together. However, the device 10 can also be made from a plurality of absorbent pieces attached together. Because the device 10 can be used on males ranging from babies to adults, the length and width can vary in size depending upon the size of a user's penis. For example, a device 10 that is about 8 inches in length and 4 inches in width can generally fit the majority of adult males. The device 10 can also be any geometric shape such as triangular, tubular or oval, so long as a penis can be inserted into the device 10.

Referring to FIGS. 2-6, the proximal end 16 of the body 12 of the device 10 includes a strip or band 24 (shown in FIGS. 5 and 6) made of a malleable material encircling a portion of the proximal end 16 thereof in order to facilitate opening and/or closing of the device 10. The band 24 is generally positioned adjacent to a top edge of the upper end 16 of the body 12 and may be attached to the outer layer 20 of the body 12 of device 10. However, the band 24 may be positioned at any location on the body 12 so long as the band 24 facilitates opening and/or closing of the device 10. Preferably, the band 24 is on an inside of the outer layer 20 for aesthetic purposes to cover the band 24 (shown in FIGS. 2 and 3); however, the band 24 can also be positioned on an outside of the outer layer 20 of the device 10 (not shown). The band 24 can be attached to the proximal end 16 of the device 10 by any means known in the art, such as using adhesive or sewing the band 24 into either of the layers 18, 20. The band 24 can be any width or diameter depending on the size of the device 10, for example, an 8 inch long device 10 can preferably have a band 24 that is approximately ½ inch in width or approximately ⅜ inch in diameter. Further, the band 24 can also be wide enough to encircle from a portion of the length of the body 12 to the entire length of the body 12 of the device 10. It is also contemplated that the band 12 may encapsulate the entire body 12 of the device 10.

Figure 2:
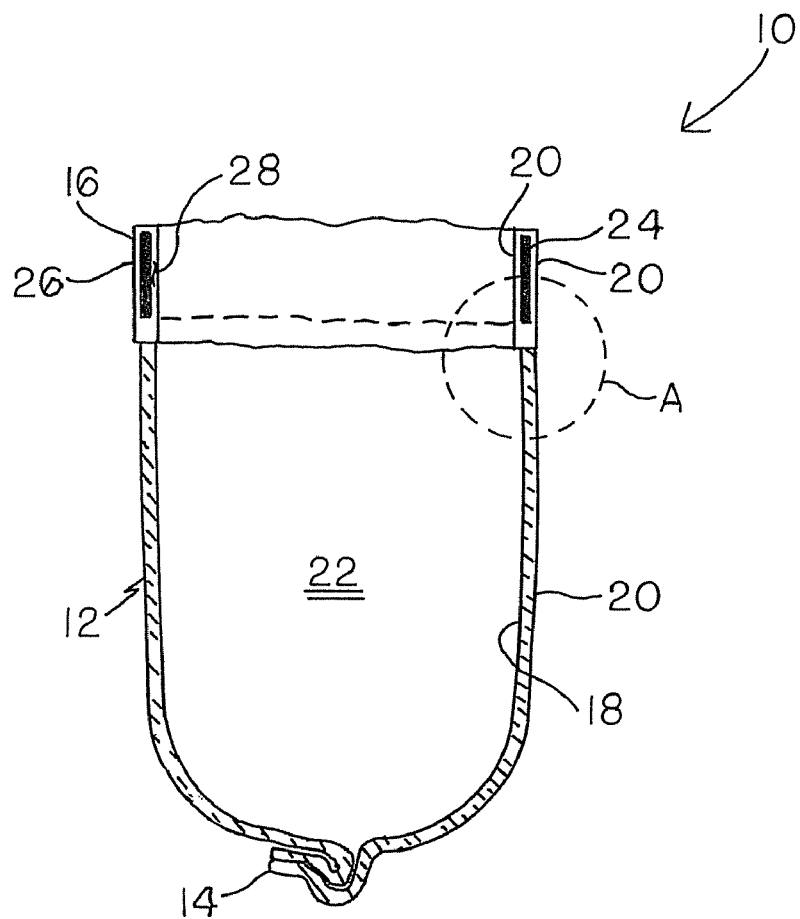
FIG. 2 is a sectional view of the male urinary device shown in FIG. 1 taken along lines II-II.
Figure 3:
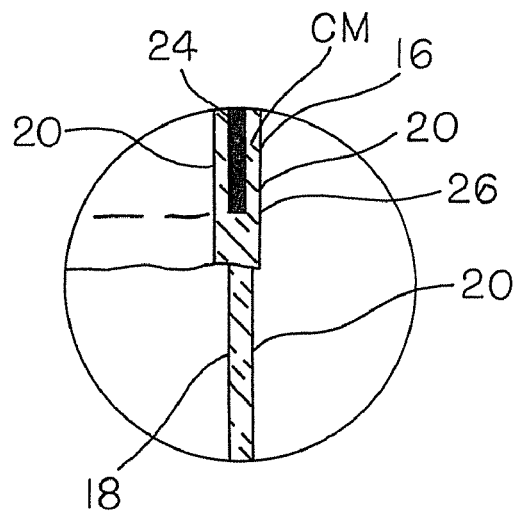
FIG. 3 is an exploded view of section A of the male urinary device shown in FIG. 2.

Referring to FIGS. 2 and 3, the device 10 may further include a neck 26 defining a hollow passageway 28 which is formed by overlapping the outer layer 20 at the proximal end 16 thereof. The band 24 may be received with the hollow passageway 28 of the neck 26 of the device 10. Also, a cushion material CM such as cotton or the like (shown as dashed lines in FIG. 3) may be positioned in the hollow passageway 28 of the neck 26 between the band 24 and the inside of the outer layer 20. The position of the cushion material CM provides additional comfort to the user's penis during closure of the band 24.

Figure 5:
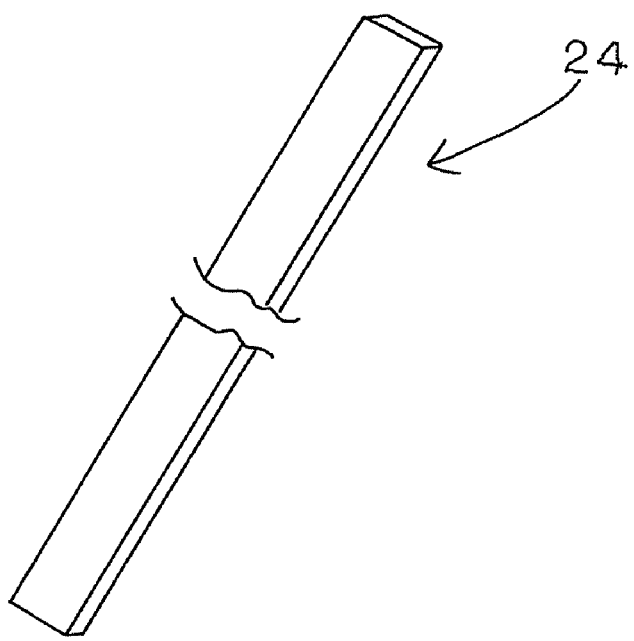
FIG. 5 is a perspective view of a rectangular-shaped band made of malleable material of the urinary device shown in FIG. 2.
Figure 6:
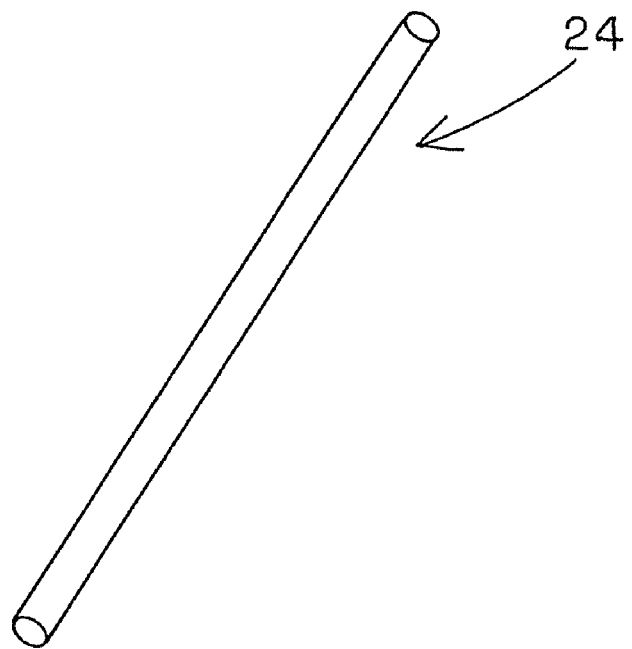
FIG. 6 is a perspective view of a circular-shaped band made of malleable material according to the present invention.
Figure 7:
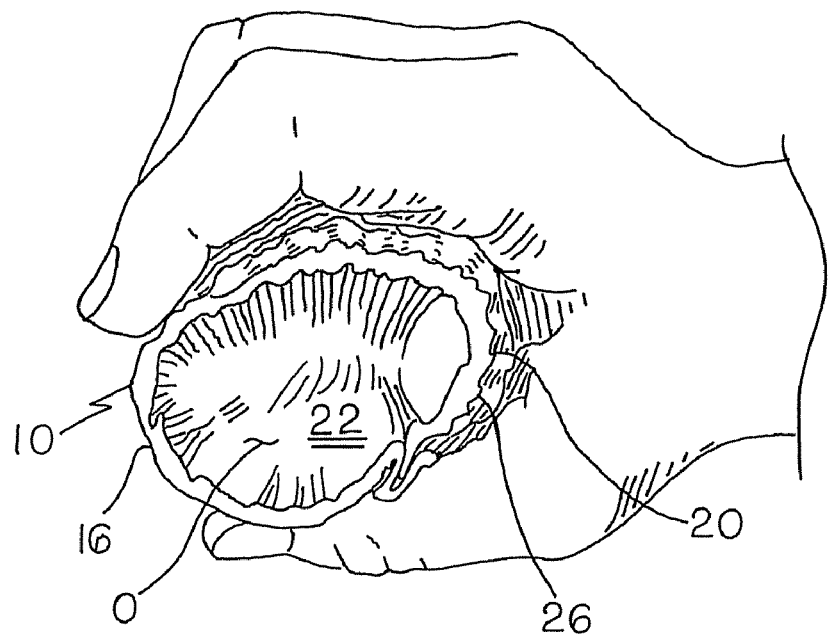
FIG. 7 shows the male urinary device of FIG. 4 in an opened position with a user's hand around an end thereof.
Figure 8:
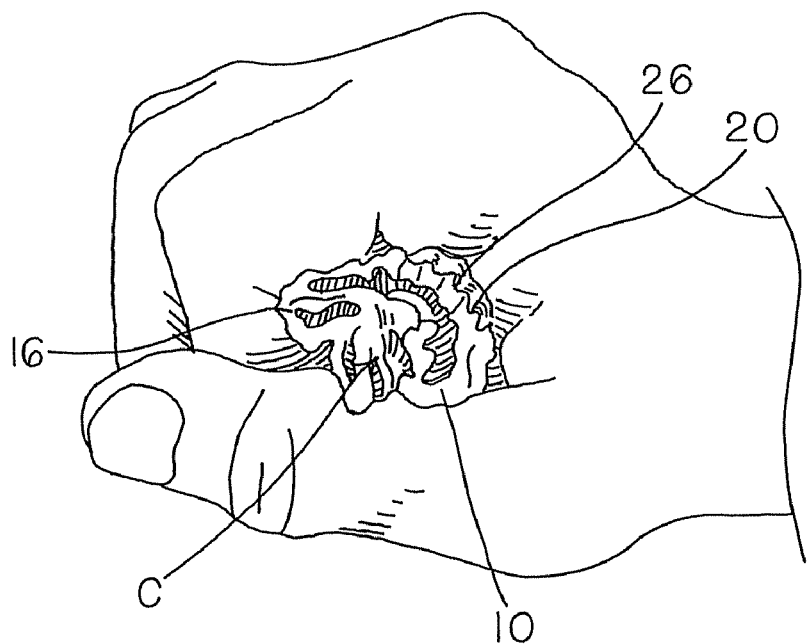
FIG. 8 shows the male urinary device of FIG. 7 in a closed position with the user's hand closed around the end thereof.

Referring to FIGS. 7 and 8 and with continued reference to FIGS. 2-6, the band 24 may be a unitary piece of malleable material or a plurality of malleable material segments encircling the proximal end 16 of the body 12 of the device 10. The malleable material of the band 24 has sufficient strength to maintain the device 10 in either an opened position O (shown in FIG. 7) or a closed position C (shown in FIG. 8). By squeezing the ends of the proximal end 16 of the device 10 in its un-wrapped position (shown in FIG. 1), the band 24 facilitates the opening of the device 10 and maintains the proximal end 16 in an opened position O as shown in FIG. 7. After the proximal end 16 of the body 12 is opened by a user's hand, the proximal end 16 retains the shape of the band 24 to conform in general to a circular shape or any other geometric shape so long as the opening is large enough for a user's penis to be inserted into the cavity 22 of the device 10. When the proximal end 16 of the body 12 is squeezed by a user's hand to close the device, the device 10 is maintained in a closed position C which conforms in general to the shape of the squeezed band 24 as shown in FIG. 8.

Referring to FIGS. 5 and 6, the band 24 can be made of a soft metal such as zinc, tin, aluminum or copper. The band 24 can be a single thin layer of malleable material or multiple overlapping layers of a malleable material. For example, the band 24 can be made of aluminum, such as multiple layers of aluminum foil that is folded, twisted or formed into a unitary piece of malleable material. Also, the band 24 can be made of a single layer of aluminum that has an appropriate thickness such that the band 24 is flexible enough to be easily bent such that the band 24 retains its shape after bending. Further, the band 24 can be made from a plurality of malleable material segments encircling the proximal end 16 of the body 12 of the device 10. The malleable material may be any material or fabricated device that can be easily bent and/or re-bent and retains its shape after being bent. Such material or device can be, for example, a malleable polymeric material or an elastomeric material reinforced with metal wire. Other malleable devices may include a hollow polymeric device (i.e., a straw) having grooves therein for bending. Also, this type of device can be filled with a liquid material or gas to help the device retain its shape when bent. The band 24 may also be any geometric shape, such as rectangular shape (shown in FIG. 5) or cylindrical shape (shown in FIG. 6).

In operation, the device 10 generally is in an un-wrapped position. The device 10 may be opened by squeezing the edges of the band 24 until the proximal end 16 opens into an opened position O. Also, other means can be used to open the device 10. When the opening is large enough for a user's penis to be inserted into the cavity 22, the device 10 is then inserted onto the penis preferably with the user's hand encircling a portion of the proximal end 16 thereof as shown in FIG. 7. When a majority of the penis is covered with the device 10, for example, the proximal end 16 is around a base of the penis, the user's hand squeezes the band 24 until the proximal end 16 closes to fit snugly against the base of the penis. Because the band 24 is malleable, the user can judge how much pressure is needed to secure the device 10 while maintaining a comfortable closure pressure on the penis. Unlike with the use of adhesive tape or Velco® fasteners, securing the device 10 of the present invention to the user's penis can be done using only one hand. After use, the device 10 is easily removed from the penis by opening the device 10 and pulling the device 10 directly away from the penis. If the device 10 has not been used to absorb fluid, the device 10 can be re-inserted back onto the penis and secured thereto.

The present invention provides for easy one-hand use of the device 10 for use on the penis of incontinent males. The device 10 absorbs urine from the penis and allows freedom of movement and prevents irritation and infection to the scrotum, inner thigh and buttocks, avoiding bed sores. The band 24 also allows the device 10 to fit snugly around the penis at the base thereof.

Further, it will be readily appreciated by those skilled in the art that modifications may be made to the invention without departing from the concepts disclosed in the foregoing description. Accordingly, the particular embodiments described in detail herein are illustrative only and are not limited to the scope of the invention, which is to be given the full breadth of the appended claims and any and all equivalents thereof.

The invention claimed is:

1. A urinary device for use on a penis of a male suffering from urinary incontinence, the device comprising:

a body having a closed distal end and an open proximal end and defining a cavity therein, wherein the body comprises an inner layer made of a moisture absorbent material and an outer layer made of a moisture resistant material; and a malleable material encircling a portion of the proximal end of the body for securing the device to a user's penis, wherein the proximal end is adapted to conform to the shape of the malleable material, wherein the malleable material comprises an elastomeric material reinforced with metal wire, wherein the proximal end of the body includes a cushion material positioned between the malleable material and the outer layer of the body, the cushion material being cotton, wherein the moisture absorbent material is a non-cotton, synthetic hydrophilic material, wherein the moisture resistant material of the outer layer at the proximal end of the body is folded to form a loop, thereby forming a neck defining a hollow passageway therein, the moisture resistant material being disposed on an outside of the proximal end of the body and on an inside of the proximal end of the body facing towards the hollow passageway, and wherein the malleable material and the cushion material are received within the hollow passageway of the neck of the device.

2. The urinary device as claimed in claim 1, wherein the malleable material has sufficient strength to maintain the device in an opened position or a closed position.

3. The urinary device as claimed in claim 1, wherein the malleable material comprises a soft metal.

4. The urinary device as claimed in claim 3, wherein the metal is selected from aluminum, zinc, copper or tin.

5. The urinary device as claimed in claim 1, wherein the malleable material comprises a thin band of material.

6. The urinary device as claimed in claim 1, wherein the malleable material comprises multiple layers of a thin band of material.

7. The urinary device as claimed in claim 1, wherein the malleable material comprises aluminum foil.

8. The urinary device as claimed in claim 1, wherein the malleable material comprises a malleable polymeric material.

9. The urinary device as claimed in claim 1, wherein the malleable material comprises a unitary band of material encircling a portion of the proximal end of the body.

10. The urinary device as claimed in claim 9, wherein the band is rectangular shaped.

11. The urinary device as claimed in claim 9, wherein the band is cylindrical shaped.

12. The urinary device as claimed in claim 1, wherein the malleable material comprises a plurality of bands of material encircling a portion of the proximal end of the body.

13. The urinary device as claimed in claim 1, wherein the device is adapted to remain in an opened position after the proximal end of the body is opened by a user's hand.

14. The urinary device as claimed in claim 1, wherein the device is adapted to remain in a closed position after the proximal end of the body is squeezed by a user's hand.

15. The urinary device as claimed in claim 1, wherein the malleable material is positioned at the proximal end on an inside of the outer layer.

16. A method of inserting a urinary device on a penis of a male comprising the steps of:

providing a urinary device comprising:
a body having a closed distal end and an open proximal end and defining a cavity therein, wherein the body comprises an inner layer made of a moisture absorbent material and an outer layer made of a moisture resistant material; and a malleable material encircling a portion of the proximal end of the body for securing the device to a user's penis, wherein the proximal end is adapted to conform to the shape of the malleable material, wherein the malleable material comprises an elastomeric material reinforced with metal wire, wherein the proximal end of the body includes a cushion material positioned between the malleable material and the outer layer of the body, the cushion material being cotton, wherein the moisture absorbent material is a non-cotton, synthetic hydrophilic material, wherein the moisture resistant material of the outer layer at the proximal end of the body is folded to form a loop, thereby forming a neck defining a hollow passageway therein, the moisture resistant material being disposed on an outside of the proximal end of the body and on an inside of the proximal end of the body facing towards the hollow passageway, and wherein the malleable material and the cushion material are received within the hollow passageway of the neck of the device;

opening the proximal end of the body of the device, wherein the proximal end remains in an opened position;

inserting the device onto a user's penis, wherein the penis is received within the cavity of body of the device; and securing the device to the penis by squeezing the proximal end of the body of the device with a user's hand, wherein the proximal end fits snugly against the penis.

17. The urinary device as claimed in claim 1, wherein the moisture absorbent material of the inner layer of the body is provided throughout the body from the closed distal end to the neck and across a width of the body on all sides of the cavity.

18. The urinary device as claimed in claim 17, wherein the device has a length of approximately 8 inches and a width of approximately 4 inches and the device is sized to cover a majority of the user's penis with the proximal end positioned around a base of the penis.

* * * * *